United States Patent [19]
Polovsky et al.

[11] Patent Number: 5,384,334
[45] Date of Patent: * Jan. 24, 1995

[54] ALKOXYLATED ALKYL GLUCOSIDE ETHER QUATERNARIES USEFUL IN PERSONAL CARE

[75] Inventors: Stuart B. Polovsky, Old Bridge, N.J.; Harold L. Moshel, Brooklyn, N.Y.; Joseph P. Pavlichko, Helmetta; Amnon Friedman, Marlboro, both of N.J.

[73] Assignee: Amerchol Corporation, Edison, N.J.

[ * ] Notice: The portion of the term of this patent subsequent to Aug. 11, 2009 has been disclaimed.

[21] Appl. No.: 927,158

[22] Filed: Aug. 7, 1992

Related U.S. Application Data

[63] Continuation-in-part of Ser. No. 447,052, Dec. 7, 1989, Pat. No. 5,138,043.

[51] Int. Cl.⁶ .............. A61K 47/00; C07H 15/00
[52] U.S. Cl. .................. 514/777; 424/47; 424/59; 536/17.2; 536/17.9; 514/23; 514/25
[58] Field of Search .............. 536/17.9, 17.2; 514/777, 23, 25; 424/47, 59, 401, 78.03

[56] References Cited

U.S. PATENT DOCUMENTS

| | | | |
|---|---|---|---|
| Re. 30,379 | 8/1980 | Gordon | 536/4.1 |
| 3,654,261 | 4/1972 | Johnson | 260/210 R |
| 3,884,977 | 5/1975 | Molnar | 260/567.6 P |
| 3,931,148 | 1/1976 | Langdon | 536/17.9 |
| 4,663,159 | 5/1987 | Brode, II et al. | 424/70 |
| 5,138,043 | 8/1992 | Polovsky et al. | 536/17.9 |

FOREIGN PATENT DOCUMENTS 0194097  9/1987  European Pat. Off. .

OTHER PUBLICATIONS

S. B. Polovsky, et al., "Alkoxylated Methyl Glucoside Quaternaries: A Series of New Raw Materials for Conditioning Shampoos", *XIVth I.F.S.C.C. Congress*, Barcelona, Spain, 1986, vol. I, pp. 335–369.

P. Alexander, "Glucose Derivatives in Cosmetics", *Manufacturing Chemist*, Sep. 1988, p. 61.

*Primary Examiner*—John W. Rollins
*Assistant Examiner*—Elli Peselev
*Attorney, Agent, or Firm*—W. K. Volles

[57] ABSTRACT

Alkoxylated alkyl glucosides having quaternary nitrogen-containing ether substituents possess cationics utility combined with extreme mildness to skin and hair along with stable personal care compositions and processes.

9 Claims, No Drawings

ALKOXYLATED ALKYL GLUCOSIDE ETHER QUATERNARIES USEFUL IN PERSONAL CARE

This application is a continuation-in-part of Ser. No. 07/447,052, filed Dec. 7, 1989, now U.S. Pat. No. 5,138,043, issued Aug. 11, 1992.

BACKGROUND OF THE INVENTION

1. Field of the Invention

This invention relates to novel glucoside derivatives, and more particularly to alkoxylated alkyl glucosides having quaternary nitrogen-containing ether substituents and to their use in personal care compositions and processes.

2. Description of Background Information

Cationics, i.e. cationic compounds such as quaternary nitrogen-containing compounds, are useful in personal care such as in conditioning hair and skin. Skin and hair adsorb cationics due to the attraction of the positive charge on the cationic with the negatively charged skin or hair surface. Cationics can penetrate wet hair and interact with structural bonds within each hair fiber. Cationics can provide lubricity to the hair which can reduce tangling during wet and dry combing. Cationics can improve the texture and softness of dry hair. Cationics can neutralize the apparent anionic charge of the hair and, therefore, eliminate static flyaway effect. Cationics provide such properties to hair based on their substantivity to the hair.

While providing such advantageous personal care utilities, cationics, however, are often toxic and irritating to the eye and skin, depending upon the particular cationic structure and concentrations. When used in higher concentrations, cationics have been known to desensitize eyes to dangerous irritation and occasionally produce corneal opacity and blindness. The utility of cationics is therefore limited by their irritation potential.

Certain glucoside derivatives, such as alkoxylated alkyl glucosides, possess mildness and low toxicity and can reduce the irritancy of cosmetic formulations. See, for example, an article by P. Alexander entitled "Glucose Derivatives in Cosmetics" in *Manufacturing Chemist*, September 1988, page 61. Cationic, alkoxylated alkyl glucosides having quaternary nitrogen-containing ester substituents combine the functionality of cationics in personal care with low toxicity and mildness associated with alkoxylated alkyl glucosides. See, for example, a preprint by S. B. Polovsky et al., entitled "Alkoxylated Methyl Glucoside Quaternaries: A Series of New Raw Materials for Conditioning Shampoos", for the XIVth I.F.S.C.C. Congress, Barcelona, Spain, 1986, Volume 1, pages 335–369. Such compounds, however, exhibit instability limiting their utility such as in personal care applications.

Other nitrogen-containing saccharide compounds have been developed. Hydroxyalkylamino and quaternary nitrogen-containing ethers of glycosides useful in cosmetic applications are described in U.S. Pat. No. 3,931,148 (Langdon). Ethereal monosubstitutions of monosaccharide derivatives useful in therapeutic compositions are described in U.S. Pat. No. Re. 30,379 (Gordon). Quaternary ammonium alkoxide alkoxy polyol compounds, including alkoxylated alkyl glucosides, useful as epoxy resin flexibilizers are described in U.S. Pat. No. 3,654,261 (Johnson).

It would be desirable if a class of compounds existed which combines the utility of cationics along with mildness and low irritancy and stability, particularly in personal care applications.

SUMMARY OF THE INVENTION

Quaternary nitrogen-containing ether substituted, alkoxylated alkyl glucoside compounds are provided represented by the structural formula:

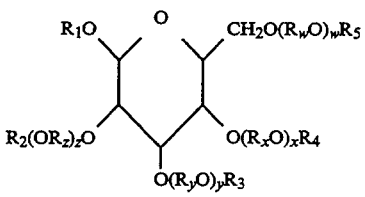

wherein:

$R_w$, $R_x$, $R_y$ and $R_z$ are ethylene or propylene;

$R_1$ is alkyl;

w, x, y and z provide an alkoxy molar substitution, i.e. MS defined by the average moles of alkoxy substituents represented by $R_{w-z}O$ in the formula as the average sum of w, x, y and z per mole of compound, of from about 1 to about 200; and $R_2$, $R_3$, $R_4$ and $R_5$ are hydrogen, an unsubstituted or oxygen-containing hydrocarbyl having from 1 to 26 carbon atoms or a quaternary nitrogen-containing group represented by the structural formula:

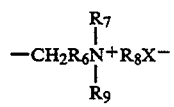

wherein:

$R_6$ is an unsubstituted or oxygen-containing hydrocarbylene having from 1 to 10 carbon atoms;

$R_7$, $R_8$ and $R_9$ are an unsubstituted or oxygen-containing hydrocarbyl having from 1 to 18 carbon atoms; and X is a halide, an inorganic anion or an organic anion having from 1 to 18 carbon atoms;

provided that at least one $R_2$, $R_3$, $R_4$ or $R_5$ is said quaternary nitrogen-containing group.

Personal care compositions and processes for managing keratinous material using compositions comprising carrier, with or without suitable personal care additives, and an effective managing amount of such glucoside compounds are also provided.

DETAILED DESCRIPTION OF THE INVENTION

Quaternary nitrogen-containing ether substituted, alkoxylated alkyl glucoside compounds of this invention possess the functionality of cationics combined with the mildness and low irritancy of alkoxylated alkyl glucosides as well as stability in personal care formulations enabling widespread utility in personal care.

The glucosidic compounds of this invention are prepared from widely available materials using standard syntheses. Glucosidic, i.e. glucopyranosidic, starting materials useful to produce such glucosidic compounds include, but are not limited to, alkyl glucosides represented by structural Formula I.

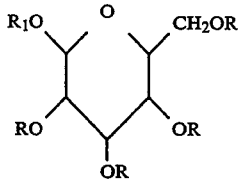

(I)

In Formula I, each R represents hydrogen or an organic substituent. The glucoside may have either enantiomeric configuration, i.e. dextrorotatory (D—) or levorotatory (L—), with D-glucoside generally preferred. The alkyl glucosides, which may be formed by reacting glucosides with alkanol under acid catalysis, have an alkyl substituent, represented by $R_1$ in Formula I, at the $C_1$ atom of the glucoside ring. Preferably, $R_1$ has from 1 to 18 carbon atoms, more preferably from 1 to 6 carbon atoms, such as, for example, methyl, ethyl, isopropyl, tertiary butyl and others. Most preferably $R_1$ is methyl. Either alkyl isomer, i.e. alpha or beta, can be used with alpha-beta blends of alkyl glucoside generally preferred. Alkyl glucosides can be reacted with alkylene oxides, using established procedures, to produce alkoxylated alkyl glucosides, wherein one or more alkoxy substituents on the C2-5 atoms of the glucoside ring are provided. Alkoxylated alkyl glucosides may be represented by the structural Formula II.

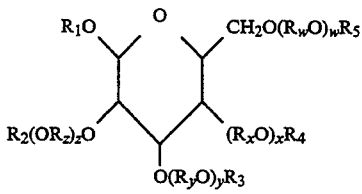

(II)

In Formula II, each $R_w$, $R_x$, $R_y$, and $R_z$ individually represents ethylene or propylene, including mixtures thereof, and preferably are all ethylene. $R_1$ is as defined previously in Formula I. The number (average) of alkoxy groups at each position is represented by w, x, y and z. The alkoxy molar substitution, i.e. MS defined by the average moles of alkoxy substituents represented by $R_{w-z}O$ in the formula as the average sum of w, x, y and z per mole of compound, is greater than 0, generally from about 1 to about 200, preferably from about 2 to about 120, and most preferably from about 10 to about 20. $R_2$, $R_3$, $R_4$ and $R_5$ individually represent: (1) hydrogen, in unsubstituted, alkoxylated alkyl glucosides; or (2) unsubstituted or oxygen-containing hydrocarbyl substituents.

The term "hydrocarbyl", as used herein, means a substituent or radical containing hydrogen and carbon atoms. The hydrocarbyl group may have any suitable structure including saturated or unsaturated, straight or branched chain, acyclic or cyclic or other structural variations and it will typically have from 1 to 26 carbon atoms, and preferably from 1 to 18 carbon atoms. Illustrative hydrocarbyl groups include, but are not limited to: alkyl, such as methyl, ethyl, isopropyl, octyl, dodecyl, octadecyl and so on; alkenyl, such as propenyl and so on; cycloalkyl, such as cyclohexyl and so on; aryl, such as phenyl and so on; and combinations like alkaryl such as nonylphenyl, aralkyl, and so on. Oxygen-containing hydrocarbyl substituents are the hydrocarbyl groups described above which also have oxygen atoms present in any suitable form such as in hydroxyl, ether, carbonyl, carboxyl, ester, heterocyclic or other oxygen-containing groups.

Illustrative glucosidic starting materials include, but are not limited to: glucose; alkyl glucosides, including ester or ether derivatives thereof, such as methyl glucoside, ethyl glucoside, methyl glucoside stearate (available as GLUCATE® SS from Amerchol Corp.), methyl glucoside dioleate (available as GLUCATE® DO from Amerchol Corp.), and other available compounds; alkoxylated alkyl glucosides, including ester or ether derivatives thereof, such as ethoxylated and/or propoxylated glucosides including methyl gluceth-10, methyl gluceth-20, PPG-10 methyl glucose ether and PPG-20 methyl glucose ether, which are the ten and twenty mole (average) ethoxylates and propoxylates of methyl glucoside, respectively (available from Amerchol Corp. as GLUCAM® E-10, GLUCAM® E-20, GLUCAM® P-10 and GLUCAM® P-20, respectively), methyl gluceth-20 distearate or PPG-20 methyl glucose ether distearate (available from Amerchol Corp. as GLUCAM® E-20 Distearate or GLUCAM® P-20 Distearate, respectively), and methyl gluceth-20 sesquistearate (available as GLUCAMATE® SSE-20 from Amerchol Corp.), and so on. Preferred glucosidic starting materials include methyl gluceth-10.

The glucosidic compounds of this invention can be produced by reacting the glucosidic starting materials with nitrogen-containing compounds as reactants. The nitrogen in such reactants may be quaternized either before or after the reaction. Such nitrogen-containing compounds may include those represented by structural Formulas III and IV.

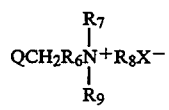

(III)

(IV)

In Formula III, Q, either alone or in combination with $R_6$, represents a functional group which is capable of reacting, either directly or after further reaction, with hydroxyl groups on the glucosidic starting materials. Illustrative functional groups Q include, but are not limited to: halides, such as chloride and others; sulfonates, such as tosylate, mesylate and others. When Q is combined with hydroxy substitution in $R_6$, compound (III) can be reacted with a base, such as sodium or potassium hydroxides or others, to form an oxirane-containing intermediate which may be represented by structural Formula V.

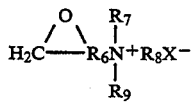

(V)

In Formulas III and V, $R_6$ represents an unsubstituted or oxygen-containing hydrocarbylene typically having from 1 to 10 carbon atoms, preferably from 1 to 4 carbon atoms; such as, but not limited to: alkylene such as methylene or ethylene and so on; hydroxy-containing alkylene such as hydroxymethylene, hydroxyethylene and so on; and other oxygen-containing hydrocarbylenes. Preferably R$_6$ is hydroxyethylene or when combined with Q represents oxyethylene having an oxirane ring formed with the adjacent carbon atom.

In Formulas III, IV and V, the nitrogen substituents, i.e. R$_7$, R$_8$ and R$_9$ represent, individually or combined, unsubstituted or oxygen-containing hydrocarbyl typically having from 1 to 6 carbon atoms, preferably having from 1 to 18 carbon atoms. Illustrative R$_7$, R$_8$ and R$_9$ groups include, but are not limited to: alkyl such as methyl, ethyl, propyl, butyl, decyl, dodecyl, hexadecyl, octadecyl and so on; cycloalkyl such as cyclohexyl; aryl such as phenyl or tolyl; or when two or more are combined with each other form a heterocyclic nitrogen-containing ring such as pyridinyl and so on. Preferably, two nitrogen substituents are methyl and one is long chain alkyl, particularly dodecyl.

In Formulas III and V, X represents an anion. Illustrative anions include, but are not limited to: halides, such as chloride, fluoride, bromide, and iodine; other inorganic anions such as sulfate or phosphate; or organic anions having from 1 to 18 carbon atoms such as mono and dibasic carboxylic acids, oxylate, citrate, tartrate, toluene sulfonate, succinate, phthalate, or others.

The glucosidic starting materials may be reacted with the nitrogen-containing reactants using established processes for producing quaternary ammonium compounds. See, for example, the procedures described in U.S. Pat. No. 3,884,977 (Molnar) or the quaternization procedures described in U.S. Pat. No. 4,663,159 (Brode, II et al.). In one method, the glucosidic starting material can be reacted with epichlorohydrin to form a chlorohydrin ether intermediate which can be reacted with a tertiary amine, as in Formula IV, to provide the quaternary derivatives. In another method, the glucosidic starting material may be reacted with halohydroxyalkyl trihydrocarbyl ammonium halide, such as 3-chloro-2-hydroxypropyl dimethyldodecyl ammonium chloride or 3-chloro-2-hydroxypropyl dimethyloctadecyl ammonium chloride, under alkaline conditions to form the quaternary derivative.

The quaternization reaction can be conducted in the presence of solvent, catalyst or other adjuvants. Typical solvents include, but are not limited to: water; inert organic compounds including lower aliphatic alcohols or ketones, such as isopropanol, butanol, acetone or others; aliphatic or aromatic hydrocarbons; and other useful solvents. Typical adjuvants to the reaction include, but are not limited to: neutralizers, such as citric, acetic, tartaric or other acids; decolorizing agents, such as molecular sieves, activated carbon, e.g. NU-CHAR® S-A or S-N, NORITE® A or SG, CALGON® RC or BL, EMERSORB® S-402 or S-404, clays, e.g. CLAROLITE® T-30 or T-60, FIL-TROL® Grade 4, 40 or 105, sodium cyanohydridoborate, sodium tetrahydroborate, hydrogen/nickel catalyst or others; filtering aids, such as diatomaceous earth; and any other useful materials.

The relative amount of nitrogen-containing reactant to glucosidic starting material is not critical and is generally at least an amount sufficient to provide measurable quaternary substitution. Typically, the molar ratio of nitrogen-containing reactant to glucosidic starting material is from about 0.05:1 to about 5:1, preferably from about 0.1:1 to about 4:1, and most preferably from about 0.2:1 to about 1:1.

The conditions under which quaternization occurs are not narrowly critical and are generally those conditions necessary to achieve quaternization. The temperature may range from at or below room temperature up to a temperature at which degradation occurs, preferably from about 40° C. to about 150° C., and most preferably from about 60° C. to about 100° C. The pressure may range from less than 1 mm Hg up to or in excess of one atmosphere, and is preferably at ambient conditions or under vacuum. The reaction may be conducted for any time necessary to achieve quaternization, generally from about one hour to about 100 hours, and most preferably from about three hours to about 48 hours.

In a typical embodiment, a reaction flask equipped with mechanical stirrer and for nitrogen atmosphere is provided with glucosidic starting material nitrogen-containing reactant, decolorizing agent and stirred at 30° C. with catalyst slowly added. The reaction mixture is then heated to an appropriate reaction temperature, typically 60° C., and allowed to react for an appropriate time, typically around 5 hours. Neutralizing agent is then added to neutralize excess catalyst. The reaction mixture is allowed to settle and the product isolated, typically using filtration with filtration aids.

The glucosidic product of this invention may be represented by structural Formula II, wherein R$_1$, R$_w$, R$_x$, R$_y$, R$_z$, w, x, y, z and X are as defined previously. R$_2$, R$_3$, R$_4$ and R$_5$ are as defined previously in Formula II with the additional provision that at least one R$_2$, R$_3$, R$_4$ or R$_5$ represents a quaternary nitrogen group represented by structural Formula VI.

In Formula VI, R$_6$, R$_7$, R$_8$, R$_9$ and X are as defined previously in Formulas III and IV, provided that R$_6$ when combined with functional group Q in Formula III represents the residue of such functional group combination.

The glucosidic product contains a level of cationic substitution, i.e. CS defined by the average moles of quaternary nitrogen-containing groups per mole of compound, of greater than 0 based on the presence of one or more quaternary nitrogen-containing groups in R$_2$, R$_3$, R$_4$ or R$_5$. CS is generally from about 0.05 up to a maximum of 4, i.e. when each R$_2$, R$_3$, R$_4$ and R$_5$ represents quaternary nitrogen-containing groups. Preferably, CS is from about 0.1 to about 4, and most preferably from about 0.2 to about 1. The glucosidic product of this invention includes mixtures of various quaternized alkoxylated alkyl glucosides alone or in combination with alkoxylated alkyl glucosides free of quaternary substitution, such as but not limited to when CS is less than 1.

Illustrative glucosidic products of this invention, generically described as alkoxylated alkyl glucose ether (oxy)hydrocarbylene tri(oxy)hydrocarbyl ammonium salts, include but are not limited to: methyl gluceth-10 hydroxypropylene dimethyloctadecyl ammonium chloride; methyl gluceth-10 hydroxypropylene dimethyldodecyl ammonium chloride; methyl gluceth-5 hydroxypropylene dimethyldocecyl ammonium bromide; methyl gluceth-5 hydroxypropylene dimethyloctadecyl ammonium acetate; methyl gluceth-20 hydroxypropylene dimethylhexadecyl ammonium chloride; PPG-20 ethyl glucose ether hydroxybutylene trimethyl ammonium bromide; PPG-10 methyl glucose ether hydroxybutylene dimethyldodecyl ammonium iodide; PPG-5 methyl glucose ether hydroxypropylene dimethyloctyl ammonium iodide; PPG-20 methyl glucose ether hydroxypropylene dimethyloctadecyl ammonium acetate; and similar compounds. Preferred glucosidic compounds of this invention are methyl gluceth-10 hydroxypropylene dimethyldodecyl ammonium chloride and methyl gluceth-10 hydroxypropylene dimethyloctadecyl ammonium chloride.

The glucosidic compounds of this invention possess a desirable balance of properties useful in personal care. As cationics, the glucosidic compounds are substantive to keratinous material such as hair and skin, providing a number of cosmetic utilities representative of cationics. The glucosidic compounds also possess mildness and low toxicity as compared to cationics in general, thereby enabling their use in cosmetic applications otherwise sensitive to cationics. In addition, the glucosidic compounds exhibit improved stability in cosmetic formulations, as compared to cationic alkoxylated alkyl glucosides having quaternary nitrogen-containing ester substituents, thereby enabling their use over a broad range of cosmetic applications.

Personal care compositions are provided comprising carrier, with or without suitable care additives, and an effective managing amount of the glucosidic compound of this invention.

The term "effective managing amount", as used herein, means an amount of glycosidic compound of this invention, or mixtures thereof, sufficient to provide a composition with personal care utility. Typically, the amount of glycosidic compound of this invention is at least about 0.05, preferably from about 0.1 to about 10, and most preferably from about 0.25 to about 2.5 weight percent of the composition. The remainder of the composition comprises carrier and any suitable personal care additives.

The carrier may be any suitable carrier, or mixture of carriers, which acts as a fluid vehicle for the composition. The type of carrier is not critical and may be selected from any carrier suitable to the particular application. Illustrative carriers include, but are not limited to: water, such as deionized or distilled water; emulsions, such as oil-in-water or water-in-oil emulsions; alcohols, such as ethanol, isopropanol or the like; glycols, such as propylene glycol, glycerine or the like; and combinations thereof. Preferred carrier systems include water-in-oil, oil-in-water or mixed water-in-oil-in-water emulsions, water, ethanol and aqueous ethanol mixtures.

Suitable personal care additives can be selected from any suitable substance which may be used to manage keratinous material, including, but not limited to, one or more of the following.

Illustrative surfactants may include: anionics including fatty acid soaps, alkyl sulfates, alkyl ether sulfates, alkyl or aryl sulfonates, sulfosuccinates, sarcosinates, alkyl glucose esters or their alkoxylates and in particular sodium lauryl sulfate, ammonium lauryl sulfate, triethanolamine lauryl sulfate, sodium laureth sulfate, alpha olefin sulfonate, disodium laureth sulfosuccinates, triethanolamine stearate; nonionics including methyl glucose esters or their alkoxylates, fatty acid alkanol amides, polyglycol ethers or their alkyl or aryl derivatives, hydroxylated lanolin, lanolin alcohols and in particular oleth-20, ceteareth-20, methyl glucose dioleate, methyl glucose stearate, glycerol monostearate, cocoyl diethanolamide, nonoxynol-7 and octoxynol-9; cationics including alkyl trimethyl ammonium salts, quaternized amides of ethylene diamine, alkyl pyridinium salts and in particular cetrimonium chloride, stearalkonium chloride and cetyl pyridinium chloride; and amphoterics including alkyl β-aminopropionates, betaines, alkyl imidazolines and in particular cocoamphocarboxy glycinate, cocamidopropyl betaine and caproamphocarboxy propionate. Illustrative cleansing oils or the like may include natural oils and alcohols and in particular mineral oil, lanolin oil, jojoba oil, sesame oil, ethanol and isopropanol. Illustrative colorants may include pigments, dyes, and in particular FD&C Blue No. 1, FD&C No. 1 Aluminum Lake or similar sets of green, red or yellow. Illustrative preservatives may include alcohols, aldehydes, p-hydroxybenzoates and in particular propylene glycol, imidazolidinyl urea, methylparaben, propylparaben, glutaraldehyde, ethyl alcohol and mixtures thereof. Illustrative moisturizers may include 2-pyrrolidone-5-carboxylic acid and its salts and esters, alkyl glucose alkoxylates or their esters, fatty alcohols, fatty esters, glycols and in particular chitosan pyrrolidone carboxylate, methyl glucose ethoxylates or propoxylates and their stearate esters, isopropyl myristate, lanolin or cetyl alcohols, aloe, silicones, propylene glycol, glycerol and sorbitol. Illustrative pH adjustors may include inorganic and organic acids and bases and in particular aqueous ammonia, citric acid, phosphoric acid, acetic acid, triethanolamine and sodium hydroxide. Illustrative emulsifiers may include anionic and nonionic surfactants and in particular stearic acid, glycerol monostearate, cocoyl diethanolamide, and the particular anionic and nonionic surfactants listed previously. Illustrative propellants may include hydrocarbons, fluorocarbons, ethers, carbon dioxide, nitrogen and dimethyl ether. Illustrative reducing agents may include hydroquinone, ammonium thioglycolate and sodium thioglycolate. Illustrative thickeners may include salts and cellulosics and in particular sodium chloride, water soluble cellulose derivatives such as hydroxyethyl cellulose, and associative thickening polymers. Illustrative sunscreen and suntan agents include para amino benzoic acid (PABA) and its esters, cinnamates, salicylates, oxybenzones and in particular ethyl dihydroxypropyl PABA, octyldimethyl PABA, ethylhexyl p-methoxycinnamate, homomenthyl salicylate and homosalate.

Other typical ingredients may include, but may not be limited to, one or more of the following: fragrances; foaming agents; depilatory agents; flavors; astringent agents; antiseptics; deodorants; antiperspirants; insect repellants; bleaches and lighteners; anti-dandruff agents; adhesives; polishes; strengtheners; fillers; barrier materials; and other personal care additives.

The amount of optional ingredients contained in the composition is not critical but will vary depending upon the particular ingredient, composition and desired use level and may be any effective amount for achieving the desired property provided by such ingredients, following established procedures.

Processes for managing keratinous material, including hair or skin, by applying the personal care compositions of this invention to keratinous material may be provided using established techniques.

The glucosidic compounds of this invention may be useful in areas other than personal care including but not limited to: health care; fabric softening; pigments; textiles; flocculation; flotation; precipitation; paints and printing inks; cleansers; oil field applications; as antistatics; as anticaking agents; as adhesion promoters; as herbicides; as corrosion inhibitors; as dispersants; as germicides; as wetting and grinding aids; as preservatives; and other areas where cationics or saccharides are useful.

Although not bound by any particular theory or mechanism, it is believed that the glucosidic compounds of this invention are useful based on a combination of factors. The presence of quaternary nitrogen in the glucosidic compound contributes cationic activity while the glucoside portion contributes mildness and low toxicity. The absence of an ester linkage between the cationic substituent and the glucoside avoids hydrolysis or saponification which would result in degradation of the compound and lead to instability, particularly under alkaline conditions used in many personal care formulations.

The following examples are presented as illustrative embodiments of this invention and are not intended to limit the scope thereof. All of the parts, percentages and proportions referred to herein, including the claims, are by weight unless otherwise indicated.

EXAMPLES

The various designations used in the examples have the following meanings. Unless otherwise indicated, all materials are available from Amerchol Corp. under the identified commercial names.

| Designation | Description |
|---|---|
| CARBOMER 1342 | A copolymer of acrylic acid and monomers containing carboxylic acid having a 1% aqueous solution viscosity of about 19,000 cps, available as CARBOPOL ® 1342 from B. F. Goodrich Co. |
| CHC N-55 | Enzymatically hydrolyzed animal protein having narrow molecular weight distribution averaging around 1,500, available as Collagen Hydrolyzate Cosmetic N-55. |
| CHPMe$_2$C$_{18}$AmCl | 3-chloro-2-hydroxypropyloctadecyl-dimethyl-ammonium chloride; available from Degussa Chemical Co. as OUAB ® 426 |
| CHPMe$_2$C$_{12}$AmCl | 3-chloro-2-hydroxypropyl dimethyldodecyl ammonium chloride, available from Degussa Chemical Co. as QUAB ® 342. |
| C$_{16}$OH&E-20 | Cetearyl alcohol and ceteareth-20 mixture available as PROMULGEN ® D. |
| C-24 | Choleth-24 and ceteth-24 mixture available as SOLULAN ® C-24. |
| EDHP PABA | Ethyl ester of dihydroxypropyl para-amino benzoic acid having UV-B absorption properties with a lambda maximum of 310 nm, available as AMERSCREEN ® P. |
| Ethyl VME/MA | Ethyl ester of vinyl methyl ether/maleic anhydride copolymer, available as UCARSET ® LP-250 Resin. |
| HEC | Hydroxyethyl cellulose having an hydroxyethyl MS of about 2, a molecular weight of about 1,000,000 and a 1% aqueous solution viscosity of 4,400–5,600 cps, available as CELLOSIZE ® Polymer PCG-10. |
| MG10HDACl | Methyl gluceth-10 hydroxypropylene dimethyldodecyl ammonium chloride having a CS of 0.25, produced as described in Example 1. |
| MG10HOACl | Methyl gluceth-10 hydroxypropylene dimethyloctadecyl ammonium chloride having a CS of 0.3, produced as described in Example 3. |
| MeG-DOE-120 | A 120-mole (average) ethoxylate of methyl glucose dioleate, available as GLUCAMATE ® DOE-120. |
| MeGeth-10 | Methyl Gluceth-10 having a hydroxyl value of approximately 360, available as GLUCAM ® E-10. |
| MeG SS | Sesquistearate ester of methyl glucoside, available as GLUCATE ® SS. |
| MeG SSE-20 | A 20-mole (average) ethoxylate of methyl glucose sesquistearate, available as GLUCAMATE ® SSE-20. |
| OE-20 | A 20-mole (average) ethoxylate of oleyl alcohol, available as AMEROXOL ® OE-20. |
| Urea/BENS | A broad spectrum preservative having a mixture of diazolidinyl urea, methyl paraben and propyl paraben in a propylene glycol base, available as GERMABEN ® II from Sutton Laboratories. |

Unless otherwise indicated, the following test procedures are used to measure product properties given in the examples.

Conditioning: The degree of conditioning is evaluated by applying the material to hair or skin, as noted, and evaluating for wet or dry feel, combing and appearance. Instron mechanical combing properties are determined based on the technique described by M. L. Garcia et al., *J. Soc. Cosmet., Chem.*, Volume 27, pages 379–398 (September 1976).

CS: The extent of cationic substitution is calculated using the following relationship:

$$CS = MW_g/(EW_Q - MW_N)$$

wherein:

$EW_Q$ represents the equivalent weight of the quaternized product, based on titration with standard sodium dodecyl sulfate and CTFA Method D30-1;

$MW_g$ represents the average molecular weight of the glucosidic starting material; and $MW_N$ represents the molecular weight of the nitrogen-containing substituent.

Saponification Value ("Sap Value"): The number of milligrams of potassium hydroxide required to neutralize the free acids and saponifiable ester groups in one gram of sample.

Hydroxyl Value: The number of milligrams of potassium hydroxide necessary to neutralize the acetic acid released upon acetylation with acetic anhydride of one gram of sample.

Irritation: A 3% aqueous solution of material, representing a typical use level in cosmetics, is evaluated using standard primary eye and dermal irritation analysis.

Acid Value: The number of milligrams of potassium hydroxide required to neutralize the free acids in one gram of sample.

Substantivity: Two techniques predictive of substantivity, i.e. adsorption on keratinous substrate, are used: (1) the Rubine Dye test, such as described by R. J. Crawford et al., *J. Soc. Cosmet. Chem.*, volume 31, pages 273–278 (September/October 1980); and (2) the "Zeta potential" measured with respect to time during a rinse cycle in an electrokinetic streaming potential analysis, such as described by E. D. Goddard, *Cosmetics and Toiletries*, April, 1987 pages 71–80.

Surface tension: Measured on a DuNouy Tensiometer using standard procedures.

Toxicity: Acute oral toxicity of undiluted (100%) material, based on standard $LD_{50}$ analysis.

EXAMPLES 1 AND 2

These examples illustrate procedures for producing glucosidic compounds of this invention. In Example 1, a single-step procedure is presented by reacting quaternary nitrogen-containing reactant with glucosidic starting material. In Example 2, a two-step process is presented in which glucosidic starting material is modified to a chlorohydrin intermediate which reacts with a tertiary amine to produce the cationic product of this invention.

Example 1

Preparation of MG10HDACl

To a reaction vessel equipped with mechanical stirring and under nitrogen blanket, 47.6 kg of MeGeth-10 and 19 kg of a 40% aqueous solution of CHPMe$_2$C-12AmCl is added and stirred while heating to 30° C. at which time 4.3 kg of 45% aqueous potassium hydroxide containing 68 g of sodium tetrahydroborate is added slowly. The reaction mixture is then warmed to 60° C. and allowed to react for five hours. Then, at 60° C., 964 g of tartaric acid is added to neutralize the excess potassium hydroxide. The reaction mixture is allowed to settle for about one hour. The lower layer of salts and water, approximately 1 kg, is removed. The upper layer is dried under full vacuum at 105°. The product is then filtered to give 51.7 kg (94% yield) of methyl gluceth-10 hydroxypropylene dimethyldodecyl ammonium chloride (MG10HDACl).

The MG10HDACl has a CS of 0.25; an hydroxyl value of 314; a nitrogen content of 0.45 weight percent; provides an ash content of 0.14%; and a 0.25% aqueous solution of the MG10HDACl gives a surface tension of 30.7 dynes/cm as well as lowering the critical micellar concentration of surfactants, and thereby reducing the potential for irritation by lowering the amount of surfactant needed when used. The MG10HDACl is soluble in water, ethanol, glycerin and castor oil and insoluble in mineral oil and isopropyl palmitate. The MG10HDACl is compatible with anionic surfactants including sodium alpha-olefin sulfonate, sodium dodecyl sulfate, sodium laureth-2 sulfate and triethanolamine dodecyl sulfate. The MG10HDACl is nonirritating to the eye based on a Draize score of 0. The MG10HDACl has moderate oral toxicity, exhibiting an $LD_{50}$ of 3.25 ml/kg of body weight. The MG10HDACl possesses a dermal irritation index of 0.17, which is classified as a nonprimary skin irritant. The MG10HDACl is substantive based on strong coloration of wool and hair switches by a 1% aqueous solution subjected to Rubine Dye analysis and strong adsorption characteristics over a 60-minute period of rinsing during electrokinetic streaming potential analysis. The material gives a residual "feel" to hair after treatment, produces a gloss or sheen on hair tresses, improves wet and dry combing based on subjective analysis as well as strongly reducing the force required during mechanical hair tress combing analysis. The MG10HDACl did not interfere with the foaming characteristics of various anionic and ampho-teric surfactants, based on a representative weight ratio of surfactant to MG10HDACl of 10:1.

Example 2

I. Preparation of Intermediate Chlorohydrin

In a round bottom flask equipped for nitrogen atmosphere, 85.7 g (0.135 moles) of MeGeth-10 is stirred and warmed to 70° C. At this point 0.3 ml of BF$_3$*etherate is added via injection and the temperature raised to 85° C. Through an addition funnel, 13.0 g (0.141 moles) of epichlorohydrin is added dropwise. The reaction temperature is increased to 95° C. and maintained for at least a half hour. The mixture is then allowed to cool to room temperature whereupon 5 g of activated alumina and 100 ml of acetone are added. The mixture is stirred for another half-hour and vacuum filtered through filter paper. The solvent is flash evaporated and the product dried in vacuum oven overnight. This gives 95.7 g (97% yield) of a straw-colored, translucent, viscous syrup.

II. Preparation of Cationic Product

In a reflux apparatus 15.4 g (21 mmoles) of the chlorohydrin adduct produced in step I, 7.5 g (35.25 mmoles) of dimethyldodecylamine and 30 ml of butanol are stirred. The mixture is brought to reflux at approximately 120° C. for 34 hours. After the butanol is distilled off at 70° C. and 100 mm Hg, the temperature is raised to 150° C. at 1 mm Hg to remove the excess dimethyldodecylamine. At room temperature enough citric acid, approximately 0.05 g, is added until a 1% aqueous solution of this mixture is at a pH of approximately 6. The mixture is then water purged at approximately 70° C. and 135 mm Hg with 6 ml deionized water. The methyl gluceth-10 hydroxypropylene dimethyldodecyl ammonium chloride thus obtained is a brick red, viscous liquid which is water soluble and as a 10% aqueous solution has a pH of 6.8. This gives 19.8 g of a dark, viscous liquid as product (96% yield). The CS of the product is 0.87.

Example 3

Preparation of MG10HOACl

MeGeth-10 (528 grams, 0.8 moles) and 252.5 grams (0.237 moles) of a 40% aqueous solution of CHPMe$_2$C-18AmCl were charged to a 2-liter neck round bottom flask equipped with a stirrer, thermometer, reflux condenser, dropping funnel and nitrogen inlet tube. A 45% aqueous KOH solution (45.9 grams, 0.38 moles) was introduced slowly through the dropping funnel into the mixture while stirring and nitrogen purging. The mixture was heated at 60° C. for five hours. Tartaric acid (about 10 grams) was added to neutralize excess KOH and adjust the pH to 6. Water was removed by heating to 110° C. with vacuum at <1 mm Hg. About 10 grams of diatomaceous earth was added to the melt at 70° C., which was then filtered. This produced 585.5 grams (97.5% yield) of clear, light brown product, MG10HOACl.

The analytical values of the product are listed below:

TABLE 1

| Ingredient | Analytical Values Amount |
|---|---|
| % Water: | 0.07 |
| % Ash: | 0.2 |
| Acid Value: | 1.30 |

TABLE 1-continued

| Analytical Values | |
|---|---|
| Ingredient | Amount |
| Sap. Value: | 2.16 |
| Hydroxyl Value: | 379.8 |
| % 1,2-Propanediol:* | 5.5 (by GC analysis) |
| CS: | 0.3 |

*1,2-Propanediol is a solvent in the CHPMe$_2$C$_{18}$AmCl sample.

EXAMPLES 4–7

Personal Care Compositions

Illustrative personal care compositions are prepared and evaluated in these examples using MG10HDACl produced as in Example 1.

Example 4

Clear Conditioning Shampoo

Clear conditioning shampoo is prepared by heating deionized water to 60° C. With propeller agitation, the additives listed in Table 1 are then added separately, waiting for each ingredient to dissolve before adding the next. When clear, the MG10HDACl is added and the composition cooled to room temperature. The formulation has a pH of 6 and a viscosity of 1700 cps.

When used in this clear shampoo, the MG10HDACl provides conditioning properties and shine to the hair.

TABLE 2

| Clear Conditioning Shampoo Formulation | |
|---|---|
| Ingredient | Amount |
| MG10HDACl | 1.00% |
| Citric acid | 0.50 |
| MeG DOE-120 | 3.50 |
| Urea/BENS | 1.00 |
| Triethanolamine-lauryl sulfate (40% aqueous) | 25.00 |
| Lauramide diethanolamine | 5.00 |
| Deionized water | 64.00 |

Example 5

Hair Conditioner

Hair conditioner containing the ingredients listed in Table 3 is prepared by adding the HEC to the water at room temperature with propeller agitation. The mixture is then heated to 75° C. When the polymer is fully hydrated, the MG10HDACl, CHC N-55, MeGeth-10 and methyl paraben, are dissolved, in that order, waiting for each to dissolve before adding the next. In a separate container, the C$_{16}$OH&E-20 and cetyl alcohol are mixed. Both mixtures are heated to 75° C. and then added together with mixing until a uniform mixture is produced, followed by cooling to room temperature with adequate mixing.

When used in this hair conditioner, the MG10HDACl, being substantive to the hair, provides for good wet combing, manageability, shine and feel properties.

TABLE 3

| Hair Conditioner Formulation | |
|---|---|
| Ingredient | Amount |
| MG10HDACl | 2.50% |
| HEC | 0.63 |
| Cetyl alcohol | 1.20 |
| CHC N-55 | 0.30 |
| MeGeth-10 | 1.00 |
| Methyl paraben | 0.15 |

TABLE 3-continued

| Hair Conditioner Formulation | |
|---|---|
| Ingredient | Amount |
| C$_{16}$OH&E-20 | 4.50 |
| Deionized water | 89.72 |

Example 6

Styling-Conditioning Mousse

Style-conditioning mousse is prepared containing the ingredients listed in Table 4 by heating the deionized water to 60° C. and then dissolving the MG10HDACl, OE-20 and Urea/BENS. This solution is then cooled to 40° C. In a separate container the Ethyl VME/MA, aminomethyl propanol and EDHP PABA are dissolved in the alcohol. The two phases are then mixed until uniform. Aluminum mousse cans are filled with this mixture and charged with A-46 propellant, i.e. a mixture of hydrocarbon propellants consisting of 80% isobutane and 20% propane, in a ratio of 95% product and 5% propellant.

When used in this styling-conditioning mousse, the MG10HDACl conditions the hair and contributes to the fixative properties of the Ethyl VME/MA to give good curl retention. In addition, the MG10HDACl plasticizes the Ethyl VME/MA for a more natural look.

TABLE 4

| Styling-Conditioning Mousse Formulation | |
|---|---|
| Ingredient | Amount |
| MG10HDACl | 0.25% |
| OE-20 | 1.00 |
| EDHP PABA | 0.50 |
| Ethyl VME/MA | 5.00 |
| Aminomethyl propanol* | 2.20 |
| SD Alcohol 40 | 15.00 |
| Deionized water | 75.05 |
| Urea/BENS | 1.00 |

*10% solution in SD alcohol 40, providing 20% stoichiometric neutralization

Example 7

Cream

Cream containing the ingredients listed in Table 5 is prepared by dissolving the CARBOMER 1342 in the deionized water and then heating the solution to 80° C. In a separate container, the MeG SS, MeG SSE-20, C-24 and cetyl alcohol are added together, heated to 80° C. and mixed until uniform. The two mixtures are then mixed together until uniform. The propylene glycol and Urea/BENS are then dissolved in the mixture. The triethanolamine is then added so that the mixture will thicken. The MG10HDACl is then slowly added to the composition while mixed until uniform. The composition is then cooled to room temperature with mixing.

When used in this cream, the MG10HDACl provides moisturizing and conditioning properties while also providing slip for ease of application.

TABLE 5

| Cream Formulation | |
|---|---|
| Ingredient | Amount |
| MG10HDACl | 2.00% |
| CARBOMER 1342 | 0.30 |
| Cetyl alcohol | 0.50 |
| MeG SS | 1.50 |
| MeG SSE-20 | 1.50 |

TABLE 5-continued

| Cream Formulation | |
|---|---|
| Ingredient | Amount |
| Urea/BENS | 1.00 |
| Propylene glycol | 5.00 |
| C-24 | 0.50 |
| Triethanolamine (10% aqueous solution) | 4.58 |
| Deionized water | 83.12 |

Example 8

Stability Analysis

The stability of MG10HDACl is compared with the stability of the chloride salt of the dimethyldodecyl ammonium acetate derivative of methyl gluceth-10 (the "ester equivalent") having a CS of 0.85, produced as described in the previously noted preprint by S. B. Polovsky et al. This latter compound has the same structure as MG10HDACl except that the quaternary substituent is connected to the glucoside by an ester linkage instead of an ether linkage. The hydrolytic stability of 10% aqueous solutions of both compounds is presented in Table 6, based on the pH of the solutions over time. The sharp drop in pH exhibited by the ester derivative indicates the ester linkage breaks apart by hydrolysis to form methyl gluceth-10 and the corresponding alcohol of the quaternary nitrogen substituent. In contrast, the pH of the MG10HDACl is essentially unchanged demonstrating long term stability.

TABLE 6

| | pH Stability* | |
|---|---|---|
| Time | MG10HDACl | Ester Equivalent |
| Initial | 5.85 | 6.86 |
| 1 Day | | 4.82 |
| 5 Days | | 3.8 |
| 6 Days | | 3.72 |
| 7 Days | 5.9 | 3.69 |
| 8 Days | | 3.42 |
| 15 Days | | 3.06 |
| 20 Days | 5.25 | |
| 22 Days | | 2.89 |
| 28 Days | | 2.9 |
| 30 Days | 5.21 | |
| 60 Days | 5.66 | |

*based on 10% aqueous solutions, at room temperature.

We claim:

1. Quaternary nitrogen-containing ether substituted, alkoxylated alkyl glucoside compound represented by the structural formula:

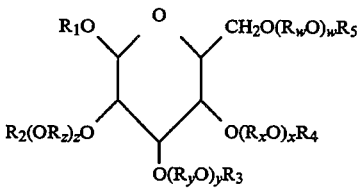

wherein:
$R_w$, $R_x$, $R_y$ and $R_z$ are ethylene or propylene;
$R_1$ is $C_{1-18}$ alkyl;
w, x, y and z provide an alkoxy molar substitution, MS, defined by the average moles of alkoxy substituents represented by $R_{w-z}O$ in the formula as the average sum of w, x, y and z, per mole of compound, of from about 1 to about 200; and $R_2$, $R_3$, $R_4$ and $R_5$ are hydrogen, an unsubstituted or oxygen-containing hydrocarbyl selected from the group consisting of alkyl, cycloalkyl, phenyl and aralkyl having from 1 to 26 carbon atoms, or a quaternary nitrogen-containing group represented by the structural formula:

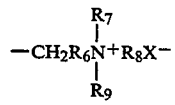

wherein:
$R_6$ is a hydroxyalkylene having from 1 to 10 carbon atoms;
$R_7$, $R_8$ and $R_9$ are an unsubstituted or oxygen-containing hydrocarbyl selected from the group consisting of alkyl, cycloalkyl, phenyl and aralkyl having from 1 to 26 carbon atoms; and
X is a halide, a sulfate anion, a phosphate anion or an organic anion selected from the group consisting of mono and dibasic carboxylic acids, oxylate, citrate, tartarate, toluene, sulfonate, succinate and phthalate having from 1 to 18 carbon atoms;
provided that at least one $R_2$, $R_3$, $R_4$ or $R_5$ is said quaternary nitrogen-containing group.

2. The compound of claim 1 wherein:
$R_w$, $R_x$, $R_y$ and $R_z$ are ethylene;
$R_1$ is $C_1$–$C_6$ alkyl;
MS is from about 10 to about 20; and
$R_2$, $R_3$, $R_4$ and $R_5$ are hydrogen or said quaternary nitrogen-containing group wherein:
$R_6$ is $C_{1-4}$ hydroxyalkylene;
$R_7$, $R_8$ and $R_9$ are $C_{1-18}$ alkyl; and
wherein the level of cationic substitution, CS, defined by the average moles of quaternary nitrogen-containing groups per mole of compound, is from about 0.05 to 4.

3. The compound of claim 2 wherein:
CS is about 0.30;
MS is about 10;
$R_1$ is methyl;
$R_6$ is hydroxyethylene;
$R_7$ and $R_8$ are methyl;
$R_9$ is octadecyl; and
X is chloride.

4. Quaternary nitrogen-containing ether substituted, alkoxylated alkyl glucoside compound represented by the structural formula:

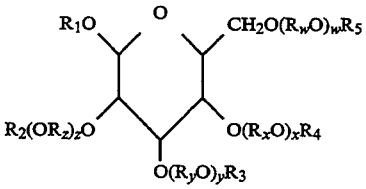

wherein:
$R_w$, $R_x$, $R_y$ and $R_z$ are ethylene;
$R_1$ is $C_{1-18}$ alkyl;
w, x, y and z provide an alkoxy molar substitution, MS, defined by the average moles of alkoxy substituents represented by $R_{w-z}O$ in the formula as the average sum of w, x, y and z per mole of compound, of from about 10 to about 20; and $R_2$, $R_3$, $R_4$ and $R_5$ are hydrogen, or a quaternary nitrogen-containing group represented by the structural formula:

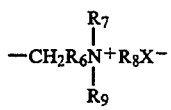

wherein:
$R_6$ is $C_{1-4}$ hydroxyalkylene;
$R_7$, $R_8$ and $R_9$ are $C_{1-18}$ alkyl; and
X is a halide;
provided that at least one $R_2$, $R_3$, $R_4$ or $R_5$ is said quaternary nitrogen-containing group; and
wherein the level of cationic substitution, CS, defined by the average moles of quaternary nitrogen-containing groups per mole of compound, is from about 0.05 to 4.

5. A personal care composition comprising a carrier and from about 0.1 to about 10 weight percent of a quaternary nitrogen-containing ether substituted, alkoxylated alkyl glucoside compound represented by the structural formula:

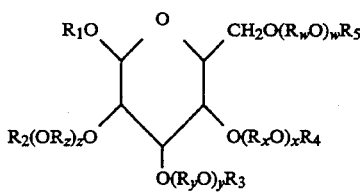

wherein:
$R_w$, $R_x$, $R_y$ and $R_z$ are ethylene or propylene;
$R_1$ is $C_{1-18}$ alkyl;
w, x, y and z provide an alkoxy molar substitution, MS, defined by the average moles of alkoxy substituents represented by $R_{w-z}O$ in the formula as the average sum of w, x, y and z, per mole of compound, of from about 1 to about 200; and
$R_2$, $R_3$, $R_4$ and $R_5$ are hydrogen, an unsubstituted or oxygen-containing hydrocarbyl selected from the group consisting of alkyl, cycloalkyl, phenyl and aralkyl having from 1 to 26 carbon atoms or a quaternary nitrogen-containing group represented by the structural formula:

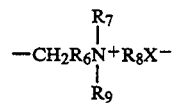

wherein:
$R_6$ is a hydroxyalkylene having from 1 to 10 carbon atoms;
$R_7$, $R_8$ and $R_9$ are an unsubstituted or oxygen-containing hydrocarbyl selected from the group consisting of alkyl, cycloalkyl, phenyl and aralkyl having from 1 to 26 carbon atoms; and
X is a halide, a sulfate anion, a phosphate anion or an organic anion selected from the group consisting of mono and dibasic carboxylic acids, oxylate, citrate, tartarate, toluene, sulfonate, succinate and phthalate having from 1 to 18 carbon atoms;
provided that at least one $R_2$, $R_3$, $R_4$ or $R_5$ is said quaternary nitrogen-containing group.

6. The composition of claim 5 wherein the carrier is selected from the group consisting of water, alcohols, aqueous alcohols, glycols, water-in-oil emulsions, oil-in-water emulsions and mixtures thereof.

7. The composition of claim 6 further comprising at least one member selected from the group consisting of a surfactant, a cleansing oil, a colorant, a preservative, a pH adjuster, an emulsifier, a propellant, a reducing agent, a thickener, a sunscreen agent, a suntan agent, a preservative and a fragrance.

8. The compound of claim 1 wherein the unsubstituted or oxygen-containing hydrocarbyl is selected from the group consisting of methyl, ethyl, isopropyl, octyl, dodecyl, octadecyl, propenyl cyclohexyl, phenyl and nonylphenyl.

9. The composition of claim 5 wherein:
$R_w$, $R_x$, $R_y$ and $R_z$ are ethylene;
$R_1$ is $C_{1-6}$ alkyl;
MS is from about 10 to about 20; and
$R_2$, $R_3$, $R_4$ and $R_5$ are hydrogen or said quaternary nitrogen-containing group wherein:
$R_6$ is $C_{1-4}$ hydroxyalkylene;
$R_7$, $R_8$ and $R_9$ are $C_{1-18}$ alkyl; and
wherein the level of cationic substitution, CS, defined by the average moles of quaternary nitrogen-containing groups per mole of compound, is from about 0.05 to 4.

* * * * *